United States Patent
Proctor, Jr. et al.

(10) Patent No.: US 11,260,164 B2
(45) Date of Patent: Mar. 1, 2022

(54) NEGATIVE PRESSURE WOUND THERAPY DRESSING AND RELATED APPARATUS

(71) Applicant: Genesis Medical Devices LLC, Indialantic, FL (US)

(72) Inventors: James A. Proctor, Jr., Indialantic, FL (US); Daniel N. Segina, Satellite Beach, FL (US)

(73) Assignee: Genesis Medical Devices LLC, Indialantic, FL (US)

( * ) Notice: Subject to any disclaimer, the term of this patent is extended or adjusted under 35 U.S.C. 154(b) by 480 days.

(21) Appl. No.: 15/674,965

(22) Filed: Aug. 11, 2017

(65) Prior Publication Data

US 2018/0078686 A1    Mar. 22, 2018

Related U.S. Application Data

(60) Provisional application No. 62/373,534, filed on Aug. 11, 2016, provisional application No. 62/373,544, filed on Aug. 11, 2016.

(51) Int. Cl.
| | | |
|---|---|---|
| *A61M 1/00* | (2006.01) | |
| *A61F 13/00* | (2006.01) | |
| *A61F 13/02* | (2006.01) | |
| *A61B 17/60* | (2006.01) | |
| *A61M 27/00* | (2006.01) | |
| *A61K 9/22* | (2006.01) | |
| *A61M 39/10* | (2006.01) | |

(52) U.S. Cl.
CPC ............... *A61M 1/90* (2021.05); *A61B 17/60* (2013.01); *A61F 13/00068* (2013.01); *A61F 13/0206* (2013.01); *A61F 13/0216* (2013.01); *A61M 1/86* (2021.05); *A61M 39/10* (2013.01); *A61M 2205/18* (2013.01); *A61M 2205/3344* (2013.01); *A61M 2205/8206* (2013.01)

(58) Field of Classification Search
CPC .... A61M 1/00; A61M 27/00; A61M 2205/18; A61M 2205/3344; A61M 2205/8206; A61F 13/00; A61F 13/02; A61F 13/00068; A61F 13/0206; A61F 13/0216; A61K 9/22
See application file for complete search history.

(56) References Cited

U.S. PATENT DOCUMENTS

| | | | |
|---|---|---|---|
| 8,034,037 B2* | 10/2011 | Adams | A61M 1/0088 604/289 |
| 2014/0107598 A1* | 4/2014 | Wudyka | A61M 1/0001 604/319 |

FOREIGN PATENT DOCUMENTS

DE        2 495 009 A1 *  9/2012

* cited by examiner

*Primary Examiner* — Tatyana Zalukaeva
*Assistant Examiner* — Ilya Y Treyger
(74) *Attorney, Agent, or Firm* — David J. Thibodeau, Jr.; VLP Law Group LLP

(57) ABSTRACT

A Negative Pressure Wound Therapy (NPWT) dressing having a sealing layer on a non-wound interfacing surface. Such a sealed surface eases application and reduces the risk of a loss of seal once applied to a patient. Associated adaptors and couplers, which may be universal couplers, allow for simplified use of the disclosed and existing dressings. An optional pressure regulator unit may use existing wall suction available in medical facilities; it may interface with a transportation unit. Embodiments of the regulation unit provide for various monitoring, operation and alarming features that may be accessed using mobile wireless, wireless LAN, and internet based connectivity approaches.

18 Claims, 12 Drawing Sheets

US 11,260,164 B2

NEGATIVE PRESSURE WOUND THERAPY DRESSING AND RELATED APPARATUS

CROSS REFERENCE TO RELATED APPLICATIONS

This application claims prioirity to U.S. Patent Application entitled "ALTERNATIVE NEGATIVE PRESSURE WOUND THERAPY APPARATUS AND METHOD WITH MULTIPLE INTERFACES" Ser. No. 62/373,534 filed Aug. 11, 2016 and also to U.S. Patent Application entitled "IMPROVED NEGATIVE PRESSURE WOUND THERAPY DRESSING AND METHOD AND ADAPTORS" Ser. No. 62/373,544 filed Aug. 11, 2016. The entire contents of each of the above-referenced applications is hereby incorporated by reference.

BACKGROUND

Technical Field

This patent is in the technical field of medical devices. More particularly, this patent is in the technical field of dressings and adaptors and/or associated regulators for is use with negative pressure wound therapy.

Background Information

The Negative Pressure Wound Therapy (NPWT) approach was significantly pioneered at Wake Forest University in the early 1990s. Aspects of this work was protected in U.S. Pat. No. 5,636,643, filed on Mar. 9, 1993 with named inventors Louis C. Argenta, Michael J. Morykwas, and assigned to Wake Forest University.

The approach has evolved over time, and generally uses sponge like material, placed into a wound and having a non-permeable covering to seal the sponge within the wound. The covering often includes an adhesive side and a non-adhesive side. The adhesive side is generally arranged to completely cover the sponge material, and to additionally make contact with the skin around the periphery of the wound. This allows for sealing of the sponge in the wound area such that a suction tube passed through, or under, the covering may be used to induce a negative pressure within the sealed area. This negative pressure produces various beneficial effects well documented in the prior art.

A number of medical device companies have commercialized this technology through the use of various sponge devices and pump devices. These companies include KCI, Genedyne, Convatec, and Smith & Nephew. These companies have supplied various sponges and vacuum pumps for use in negative pressure wound therapy. Examples of a sponge and associated negative pressure method are described in U.S. Pat. No. 6,695,823, assigned to KCI Licensing Inc. An example of a vacuum pump for use with the negative pressure approach which enables portability, is included in U.S. Pat. 6,142,982, assigned to KCI Medical Limited, and includes a pump connected to the suction tube for producing the negative pressure, as well and other specific elements. A number of medical device companies have commercialized this technology through the use of various sponge devices and pump devices. Such a portable vaccum pump is shown in the prior art FIG. 9 of U.S. Pat. No, 6,695,823.

As mentioned in the prior art, and in use in the industry, the suction unit which in the prior art include pump units, require specific features to improve the effectiveness, safety and reliability of the negative pressure wound therapy. These features include, the regulation of the pressure from the pump, pre-programmed pressure profiles which vary with time, and importantly various alarms to indicate a number of negative situations. Some important alarm indications include: the fluid reservoir being full; a loss of the seal of the dressing indicating a loss of suction and negative pressure; a loss of power to the pump unit; or a low battery indication if battery powered.

The other previously mentioned device companies also supply suction units, sponge dressings, and associated connection accessories including tubing and proprietary adaptors for fitting to their sponges and pump units.

SUMMARY

The previously mentioned device companies also supply sponge dressings, and associated connection accessories including tubing and proprietary adaptors for fitting to their sponges and pump units. However, there are a number of significant issues with the current arrangement of devices and dressings, and their use within hospitals and other treatment centers.

A significant issue with the existing approaches is that a negative pressure to dressing, dependent of the manufacturer, requires a specific and compatible suction unit to supply the suction, and specific tubing and adaptors.

Furthermore, existing dressings require the medical professional to first apply the sponge material, then apply a airtight film over the entire top for the sponge material. is The application of the adhesive airtight film, over the sponge material is cumbersome and is prone to errors due to the film sticking together, or being placed incorrectly, or losing the integrity of the seal.

Thus, one advantage provided by the approaches herein is an alternative dressing which simplifies the application process for the medical professional. Another aspect is to provide an adaptor which allows for compatibility between one or more manufacturers dressings and one or more alternative manufacturer's suction source unit, which is capable of interfacing to the dressings from multiple manufacturers to avoid the management of multiple inventories. Another aspect is to provide for an adaptor approach to simplify the use of external fixator rods as are commonly used within orthopedics, with existing or the improved negative pressure dressings.

There are also a number of significant issues with the current arrangement of devices and dressings, and their use within hospitals and other treatment centers.

One significant issue with the existing approach is that a negative pressure dressing, dependent of the manufacturer, requires a specific and compatible suction unit to supply the suction, alarming function, and other desirable features. Such units are generally only compatible with dressings from the same manufacturer, and further require power in order to operate, or to charge their batteries. This arrangement has negative impact to the operation of a treatment center due to: the management of multiple compatible inventories of pump units and dressings; the management of the charging of the batteries associated with battery powered pump units, the availability of electrical power in some of the locations which are desirable for use of such pump units.

Thus, among several advantages is the ability to provide for an alternative suction source unit which is capable of interfacing to the dressings from multiple manufacturers to avoid the management of multiple inventories. Other advantages are to provide for an alternative suction source unit which reduces the need for the management of multiple suction sources or pump units in the inventory of the treatment center. Other advantages are to provide for an alternative suction source unit with reduced operational expenses, providing for a reduced power consumption of a suction source unit, or other operational costs as charged by the manufacturer for hourly operation for currently deployed suction units.

It is an object to provide for an Improved Negative Pressure Wound Therapy Dressing. It is a further object to provide for a Universal Coupler for suction source with NPWT which allows for interfacing dressings and suction sources from different manufacturers. It is a further object to provide for a External Fixator Adaptor for NPWT Dressing, which allows for a simplified application and sealing of the fixator within the dressing.

One embodiment provides for a system and method for an improved Negative Pressure Wound Therapy (NPWT) dressing and associated adaptors and couplers. It is envisioned that at least some of the associated adaptors and couplers may be used with existing NPWT dressings to provide for improvements in ease of use, reduction of application time, and cost reduction due to reduced inventory items.

In an embodiment of the dressing, an air tight material is applied to the top of the sponge material. Such a sealing layer may be a plastic, rubber, or other coating commonly used in the industry. The sealed top surface of the sponge or open celled foam material may be trimmed by the medical professional during application, leaving the sides non-sealed. The sides of the sponge material may require sealing as well for the NPWT process or work. Such sealing may be achieved using a adhesive tape, which is impermeable. The tape may also allow for mechanical security of the sponge to the patient. Such a sponge with a top sealed surface allows for a reduced complexity of application of the dressing, as only the sides of the sponge material need be sealed, and any other punctures through the surface of the sealed surface. As with the edges of the sponge, the punctures for the suction tubing, or external mechanical fixators, may be sealed using an air tight adhesive tape.

In another embodiment, the punctures of the sealed surface for fixators, tubes, and the like, may be sealed using specialized adaptors to ease the sealing process. Such adaptors may themselves be attached with tape, or may have an adhesive layer applied to the surface of the adaptor which comes into contact with the sealed surface of the sponge. Such embodiments of the adaptors may further be used with existing sponges, sealed as in conventional approaches (with the adhesive film).

In embodiments, the combination of the sealed sponge using adhesive tape or strips of tape greatly reduces the complexity of the medical professional's application of the dressing.

In another aspect and embodiment, a universal coupler is provided to allow the interfacing of dissimilar suction tubing, allowing dressings and suction sources from differing manufacturer to interoperate.

In another embodiment, a negative pressure wound therapy sponge design has a Non-wound contacting surface with a sealing layer preventing the passing of gas or liquids. The edges of the sponge is trim-able in this arrangement, thereby allowing for the correct fitting to a wound, leaving the trimmed edges non-sealed. A sealing substance may be used for sealing from the top the sponge, covering the non-sealed sides of the sponge, to the patents epidermis.

In another embodiment, a negative pressure wound therapy sponge design includes a Non-wound contacting surface having a sealing layer for preventing the passing of gas or liquids, where the sealing substance is a tape including a protective layer, such protective layer being removed prior to application, and exposing an adhesive for the connecting of the tape to one or more of the top of the sponge, to the patient, and another section of tape. The adhesive in another, non-limiting example is an adhesive such as that used with EKG leads or the like.

In another embodiment, the top (sealed) side of the sponge includes a suction hose interface port, from interfacing the sponge to the suction hose.

In another embodiment, the top (sealed) side of the sponge is used to interface to a suction hose by a puncture in the sealed surface applied during application.

It is therefore an object herein to provide for an apparatus, system and method to provide for an improved negative pressure wound therapy dressing and associated couplers, adaptors, interfaces and the like. The result is an improvement such at the dressing may lose seal less often than is common currently in the industry. Further embodiments allows for a reduction of the application time of the dressing from 10 to 20 minutes, to 5 minutes or less. Finally, embodiments allow for the application and use of NPWT in difficult anatomical contours, which is not practical currently.

One embodiment may provide for a regulation unit and assembly which includes a source port for connecting directly or indirectly to existing wall suction, currently available broadly in treatment centers and particularly within hospitals. The regulation unit source port may be compatible with standard interfaces such as those defined in ISO 10079-3:2009 Compliant Suction Interface Probe. In this embodiment the regulation unit also has a dressing port for connecting either directly or indirectly to one or more negative pressure wound therapy (NPWT) dressings, and a fluid reservoir associated with the regulation unit (either integral or via a sink port). The unit further includes a control interface, and alarm function. In this embodiment, the regulation unit regulates pressure between the wall suction port and one or more of the dressing port and a NPWT Dressing.

The regulation unit is further for maintaining a pressure profile at the one or more of the dressing port and a NPWT Dressing. The pressure profile may be maintained at a constant pressure level, or alternatively the pressure profile may have a predetermined pressure level which varies with time in a pre-determined manner. In another embodiment the pressure profile may be dependent on external variables including one or more of: the amount of suction resistance on one or more of the dressing port and a NPWT Dressing; the fluid level in the reservoir; the fluid drainage rate; an input from an automated IV drug dispenser; input from a blood pressure monitoring device; or information received via a wireless sensor. In another embodiment such inventive profile features may be incorporated into suction units including internal pump devices, in addition to or as an alternative to the regulation unit of the first embodiment.

In one embodiment, the regulation unit may further include alarm functions, which are standard in prior art products but customized for use with a regulation unit rather than a unit incorporating a pump. Other alarm functions which may be included in the regulation unit of the first embodiment would indicate: the loss of wall suction below a pre-determined threshold; a loss of seal associated with one or more of the sink port, the NPWT Dressing interface, and/or related interconnections; a condition of an internal reservoir; and/or a condition of an external reservoir, such indication determined by use of an external detection apparatus.

In an embodiment, the regulation unit may have a control interface, where the control interface performs one or more of the following functions: inputting a known pressure level or profile; displaying information related to the current pressure and the pressure profile; storing and/or retrieving pressure profiles; retrieving alarm information; retrieving monitored pressure regulation performance parameters; and/or display of the status or other information, where the status display is a LCD display or other display.

In another embodiment, the interconnection between the dressing port and the NPWT dressing includes an adaptor, where the adaptor is for adapting between a connection to the sink port and a connection to two more NPWT dressings with differing connection interfaces such as those from different manufacturers. An alternative embodiment of the adaptor provides for two or more adaptors being interchangeable for adapting between a connection to the dressing port and a connection to one of two more NPWT dressings with differing connection interfaces. The adaptor may also provide for adapting between a connection to the dressing port and a connection to two more NPWT dressings (multiple dressing interface).

In another embodiment, the reservoir may be located internally to the regulation unit and assembly, while in a yet another embodiment the reservoir is located external to the regulator and control unit.

With regard to the control functions of one embodiment, the functions may be accessed remotely via an Internet Protocol (IP) based connection, a web interface, or the other protocols and including mobile telephony based techniques.

In another embodiment of the alarm functions, alarm notification may be provided using one or more of SMS, instant message, text message, email, or other electronic notification approaches.

Additionally, in yet another embodiment, the regulation unit of the first embodiment may interface to a second transportable unit, and provide a suction source to the regulation unit. This embodiment may allow for the combination of the regulation unit and the suction unit to provide the desired operation and be transportable and operate on battery, or other power source. In one embodiment of the transportable suction unit, the regulation unit is modular and fits in an integral way, with the housing of the transport suction unit. Regardless, the transport unit may replace the suction source of the first embodiment (the wall based suction interface in some embodiments), with the suction source provide by the transport unit.

The above summary, the enclosed figures, and the following description provided within this application are intended as non-limiting examples of embodiments. This application is intended to cover alternatives and variations of these example embodiments as well.

BRIEF DESCRIPTION OF THE DRAWINGS

The description below refers to the accompanying drawings, of which.

DETAILED DESCRIPTION OF ILLUSTRATIVE EMBODIMENTS

Figure 1:
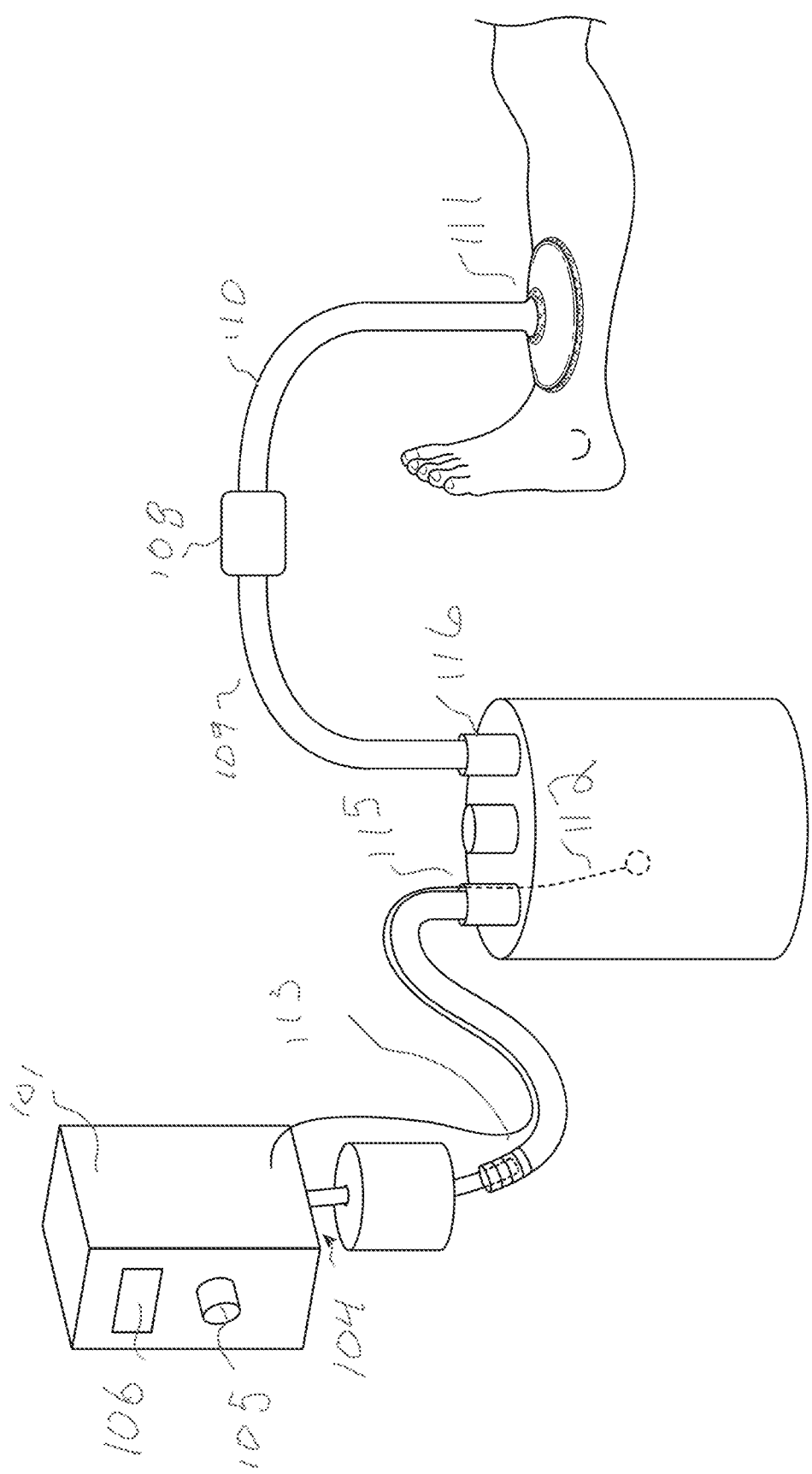
FIG. 1 is a diagram of a Negative Pressure Wound Therapy (NPWT) system utilizing the sealed sponge dressing(s) described herein.

FIG. 1 is a diagram of a Negative Pressure Wound Therapy system, which may be similar to those disclosed in U.S. Patent Publication 2013-0045360, hereby incorporated by reference. FIG. 1 shows a regulator unit 101 which provides regulated suction to sink port 104, interfacing to hose assembly 113. The suction regulation control and other features may be set by control knob 105, with alarms and current status displayed using display 106. Sink port 104 interfaces to reservoir 105 via tube assembly 113 including a safety trap, via reservoir port 115. The safety trap is used for catching liquids that have to passed through the reservoir 107 to prevent the introduction of liquids into regulator unit 101. In an embodiment, a reservoir unit 107 interfaces to an embodiment of a universal coupler 108 via hose 109 and reservoir port 116. Universal coupler 108 provides for a common interface from the reservoir 107 and hose 109 to suction hose 110 provided by various manufacturers with differing interfaces. In an alternative embodiment, universal is coupler 108 may interface to reservoir 107 directly, thereby omitting suction hose 109. Suction hose 110 interfaces to negative pressure dressing 111, which may be an embodiment of the improved dressing or a conventional dressing as known in the art. In an alternative embodiment reservoir 107, coupler 108 may be integral with regulator unit 101 including safety trap hose assembly 113, or in some embodiments, with hose 109. Fluid level probe 112 is used to sense the fluid level in reservoir 107 and is monitored by regulator unit 101 and may alarm if fluid level is too high.

Figure 2:
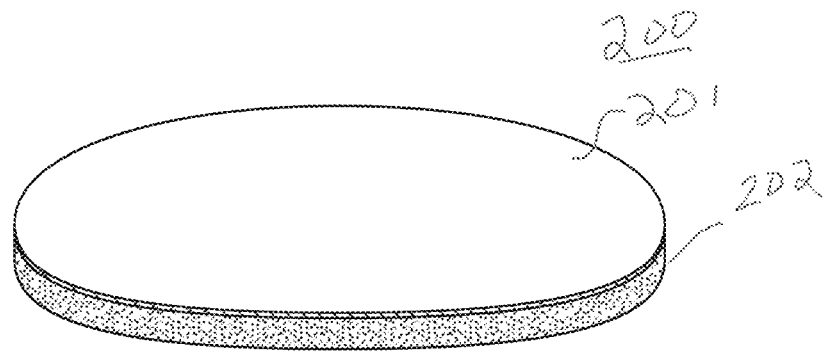
FIG. 2 is a diagram of an embodiment of the sponge dressing with a sealed top surface, unused with no suction applied.

FIG. 2 is a diagram of an embodiment of an improved sponge dressing with a sealed top surface, unused, and with no suction applied. Improved sponge dressing 200 is comprised of a sealed surface away from the wound interface, using sealing material 201. Such sealing material may be a surface layer 201 and may be composed of any flexible sealing material which prevents and/or limits the passing of liquids or gas. Such materials may include plastics, rubbers or other materials known in the art. Dressing sponge material 202 may be a foam or sponge material allowing the passing of liquids or gas and may be constructed of a layer of open celled foam or the like, as known in use in the industry. Sponge layer 202 and non-wound contacting sealing layer 201 may be bonded together to form an integral structure. Prior to application, improved dressing 200 may be trimmed to the correct shape for the surface of a wound area for application of pressure wound therapy. Such trimming may leave the sides of the dressing unsealed, but the non-wound contacting surface 201 remains sealed.

Figure 3A:
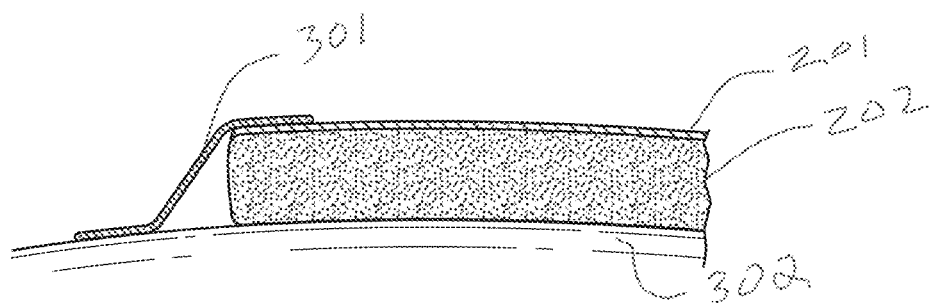
FIG. 3A is a diagram showing the use of the dressing with a sealed top surface.

FIG. 3A is a diagram showing the use of the dressing with a sealed top surface. Application of trimmed dressing to patient wound 302 may be sealed using tape 301. Such tape does not allow the passing of liquid or gas and is commonly used with various applications in the medical industry. Alternatively, an improved sealing tape may be used as an aspect, which utilizes adhesives common to that used with EKG lead patches, as known in the art.

Some examples of commercially available EKG leads with suitable gel-type is adhesives include 3M's Red Dot® Monitoring Electrodes, Medi-Trace® 530 Series Adult Hydrogel Electrodes, and Covidien® Medi-Trace 130 Mini Monitoring Infant Electrodes. The adhesives discussed in co-pending U.S. patent application Ser. No. 15/438,911 filed Feb. 22, 2017 entitled "Apparatus and Method for a Temperature Released Adhesive Structure for Use with Bandages", incorporated by reference herein, may also be suitable.

The adhesive may be applied after the integral structure is trimmed to fit the wound. Here the adhesive may be provided in a separate container, such as a squeeze tube, spread around the area of the wound before the integral structure is applied. The adhesive may also be used in other places, such as around the shaft of the hose, an external fixer, or the external implant. The adhesive may also be used in other places, as will be understood from the discussion that follows, such as around the shaft of a hose, an external fixer, suction source, or the external implant (e.g. rods, nails, wires, screws, fixitors, or the like.).

Figure 3B:
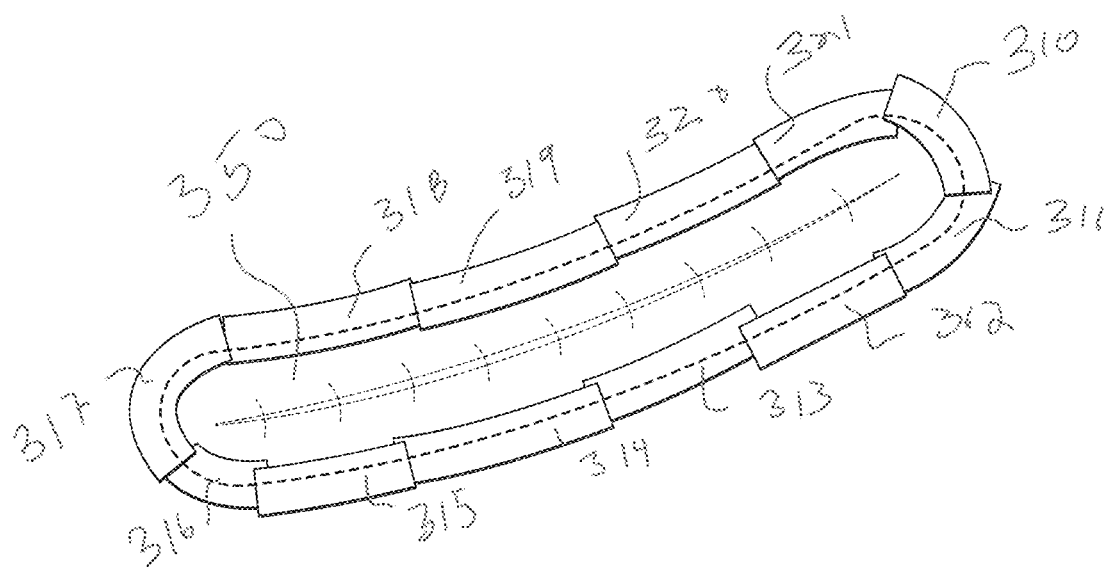
FIG. 3B is a diagram showing the top view of the use of the dressing with a sealed top surface and sealed edges using tape.

FIG. 3B is a diagram showing the top view of the use of the dressing with a sealed top surface and sealed edges using tape. In a non-limiting example, a top view of the application of sealing tape 301 to the dressing is shown. Segments of sealing tape 310 to 321 may be applied in overlapping strips to the unsealed edges of the improved dressing 350, having a sealed non-wound side of the dressing.

Figure 3C:
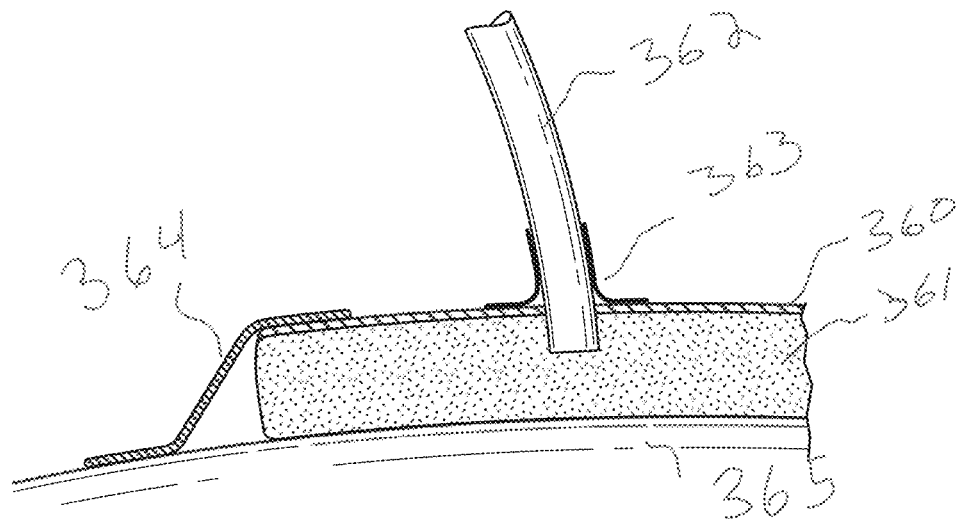
FIG. 3C shows use of the dressing with suction hose inserted through the sealed surface.

FIG. 3C shows use of the improved dressing with suction hose inserted through the sealed surface. Suction hose 362 enters through NPWT dressing sealed surface 360 into sponge material 361. Sealing tape 363 may be used to seal the hose dressing interface. The edges of the dressing may also be sealed using sealing tape 364, sealing between sealed surface 360 and patient epidermis 365.

Figure 3D:
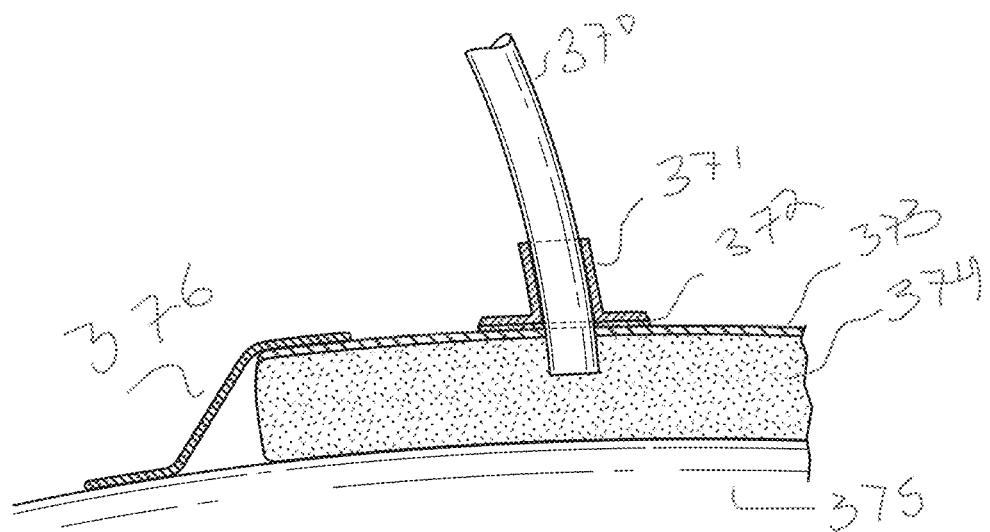
FIG. 3D shows use of the dressing with suction hose inserted through the sealed surface with a suction hose interfacing adaptor.

FIG. 3D shows use of the improved dressing with suction hose inserted through the sealed surface with a suction hose interfacing adaptor. Adaptor 371 may be used to is seal the hose 370 interface to sealed surface 373. The adaptor may be sealed to the sealed surface 373 using adhesive layer 372. Suction hose 370 is interfaced to adaptor 371 with either adhesive or sealing gel or mechanical tension fit, such that suction is maintained. Dressing sponge material 374 may be sealed to patient 375 using sealing tape 376.

Figure 4A:
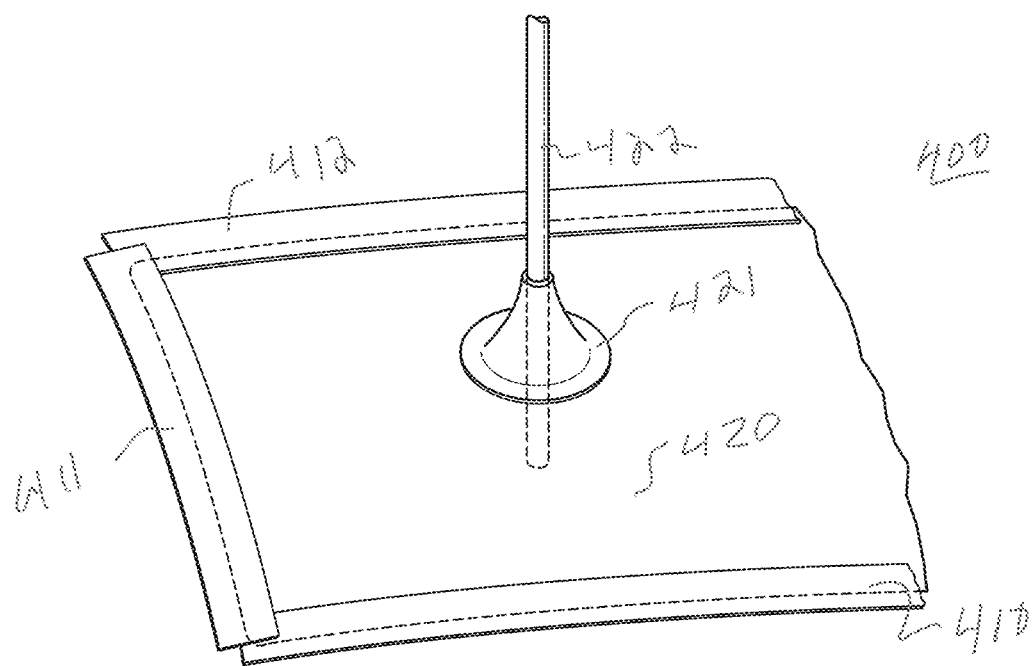
FIG. 4A is a top view of use of the dressing with suction hose inserted through the sealed surface with an adaptor for use with a fixator.

FIG. 4A is a top view of use of the improved dressing with a suction hose inserted through the sealed surface with an adaptor for use with a fixator. External fixator 422 is interfaced to NPWT sealed surface layer 420 using adaptor 421. Sealing tape 410 may be used to seal the non-sealed edges of the dressing form the sealed surface layer 420 to the patent allowing for a negative pressure to be maintained.

Figure 4B:
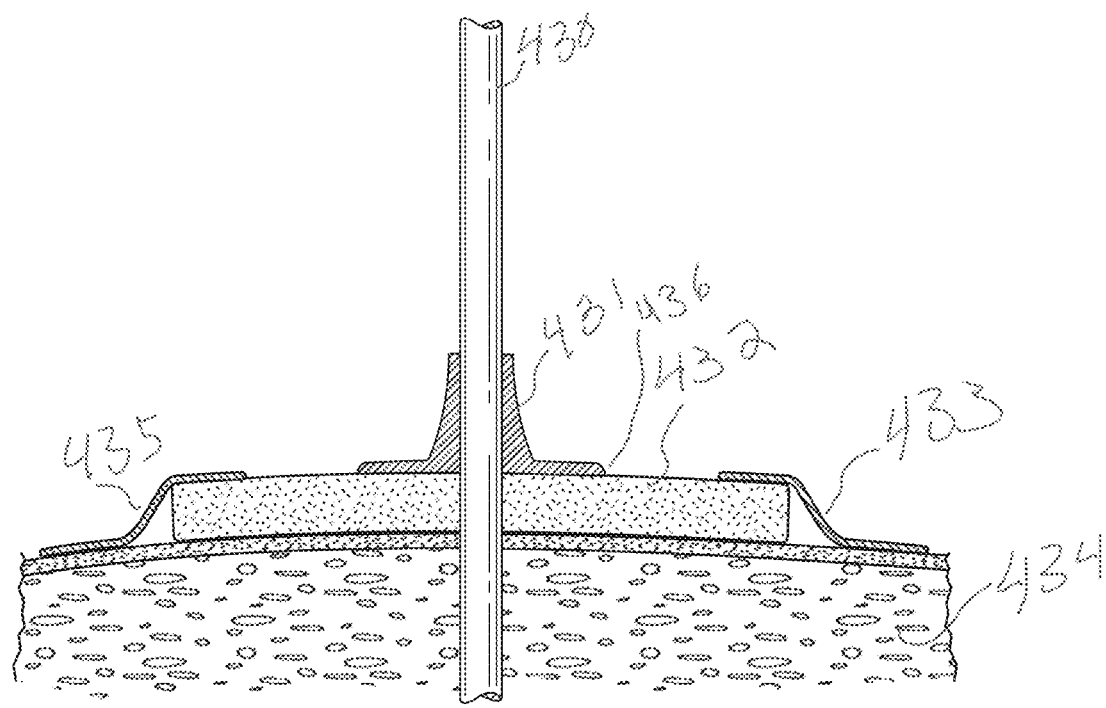
FIG. 4B is a side view of FIG. 4A, showing application to a patient.

FIG. 4B is a side view of FIG. 4A, showing application to a patient. External fixator 430 is interfaced to dressing 432 using fixator adaptor 431 with adhesive surface 436, making an air-tight seal between the fixator and the dressing sealed surface. Sealing tape 433 may be used to seal between dressing sealed surface and patient 434.

Figure 5A:
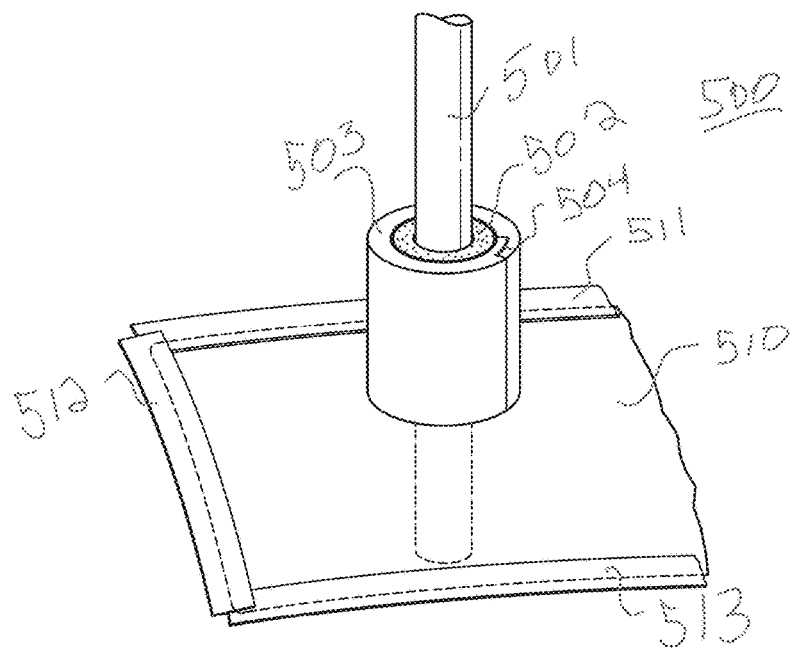
FIG. 5A shows use of an alternative fixator adaptor.

FIG. 5A shows use of an alternative fixator adaptor. Alternative fixator adaptor is comprised of plastic or other suitable material 503, gasket or foam material 502 used to maintain seal between fixator 501 and sealed surface 510. Clasp 504 is shown in a closed position said clasp used in open position for allowing adaptor to be applied to fixator when fixator is already in position. Either adhesive layer or sealing tape may be used to maintain a seal between adaptor structure 503 and sealed surface 510. Seal from patient to seal surface 510 of the dressing is maintained using sealing tape 511, 512 and 513.

Figure 5B:
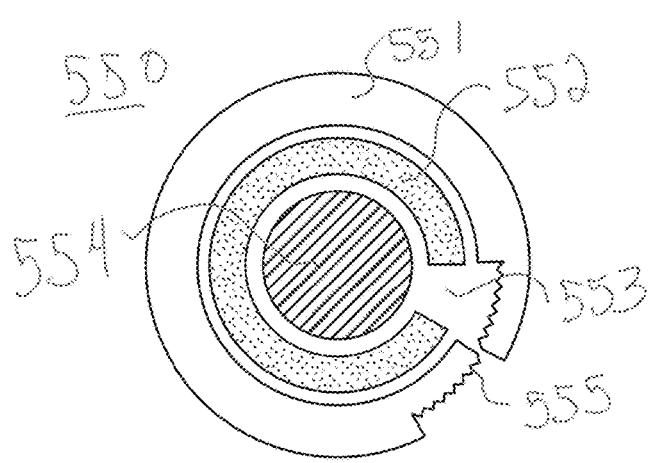
FIG. 5B shows a cross view of a fixator adaptor in open position.

FIG. 5B shows a cross view of a fixator adaptor in open position. Gap 553 is used to allow application of adaptor 550 to fixator 554. Adaptor structure 551 allows for compression of sealing gasket material 552 around fixator 554. Closure of adaptor structure 551 and tension is maintained using clasp teeth 554.

Figure 5C:
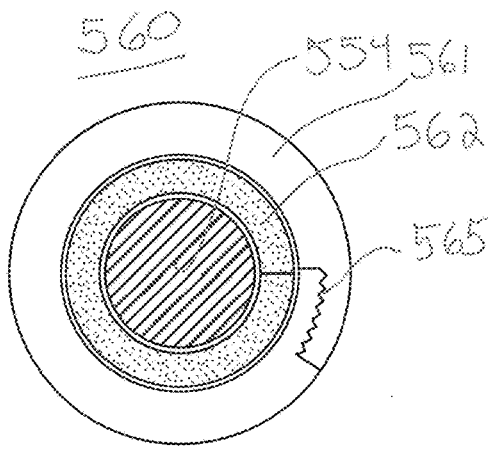
FIG. 5C shows a cross view of a fixator adaptor in closed position.

FIG. 5C shows a cross-sectional view of a fixator adaptor in closed position. Fixator 554 is encompassed by gasket material 562 and compressed by adaptor structure 561 having mechanically adjustable diameter. Tension and compression is created by clasp 565.

Figure 5D:
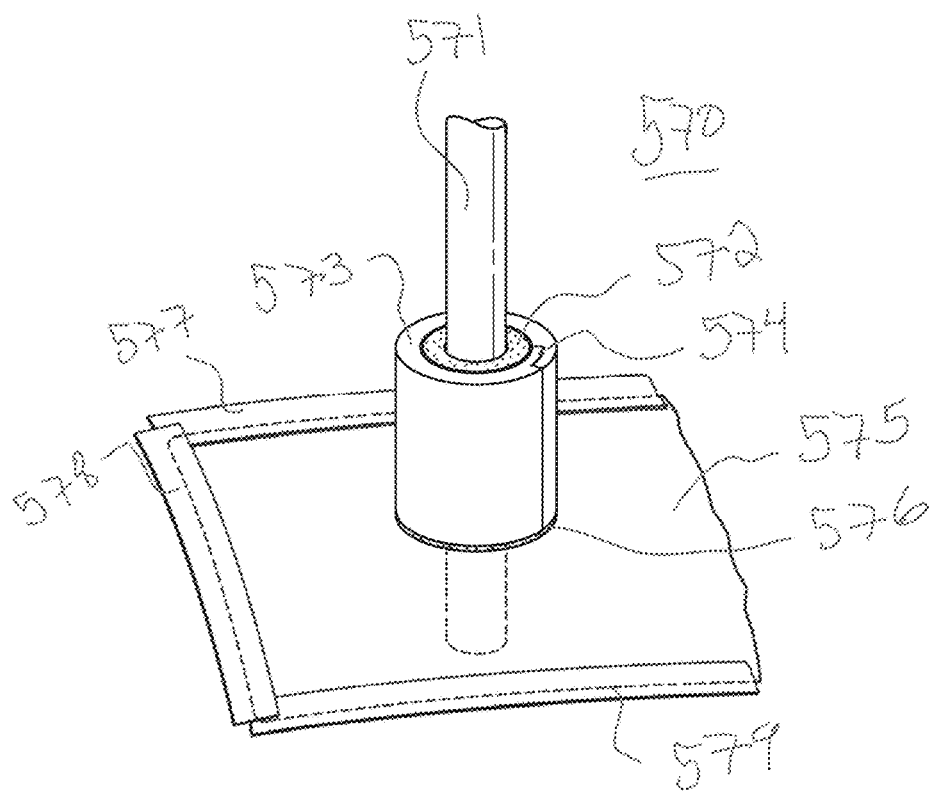
FIG. 5D shows fixator adaptor with adhesive bottom interface.

FIG. 5D shows a fixator adaptor with adhesive bottom interface. Sealing adhesive layer 576 is used to maintain a seal between adaptor 570 and dressing sealed surface 575. Adaptor 570 is comprised of adaptor structure 573, gasket material 572 and clasp 574 and adhesive layer 576. External fixator 571, using adaptor 570, maintains an air-tight seal to sealed surface dressing 575. Sealing tape 577, 578 and 579 may be used to maintain a seal between sealed surface layer 575 and the patient.

Figure 5E:
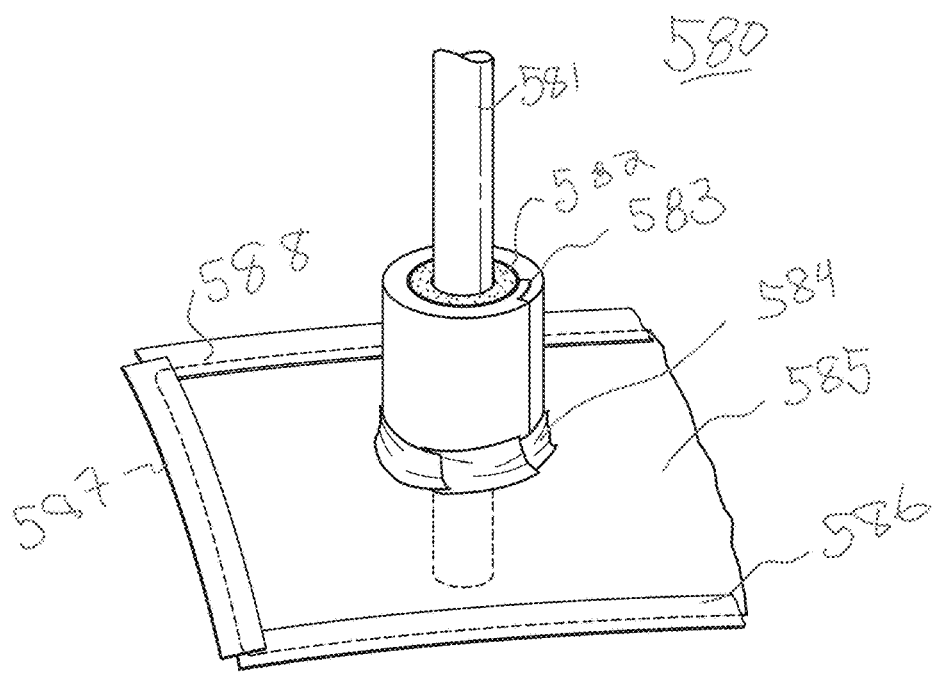
FIG. 5E shows fixator adaptor with taped interface.

FIG. 5E shows fixator adaptor with taped interface. In an alternative embodiment, rather than using adhesive layer 576, sealing 584 may be used to maintain a seal from adaptor structure and sealed surface layer 585. Fixator 581 may maintain a suction seal using adaptor 580, despite puncturing sealed surface layer 585. Adaptor 580 is comprised of adaptor gasket material 582 and adaptor mechanical clasp 583 and structure 573. Dressing surface 585 may be sealed to patient using sealing tape 586, 587 and 588.

Figure 6A:
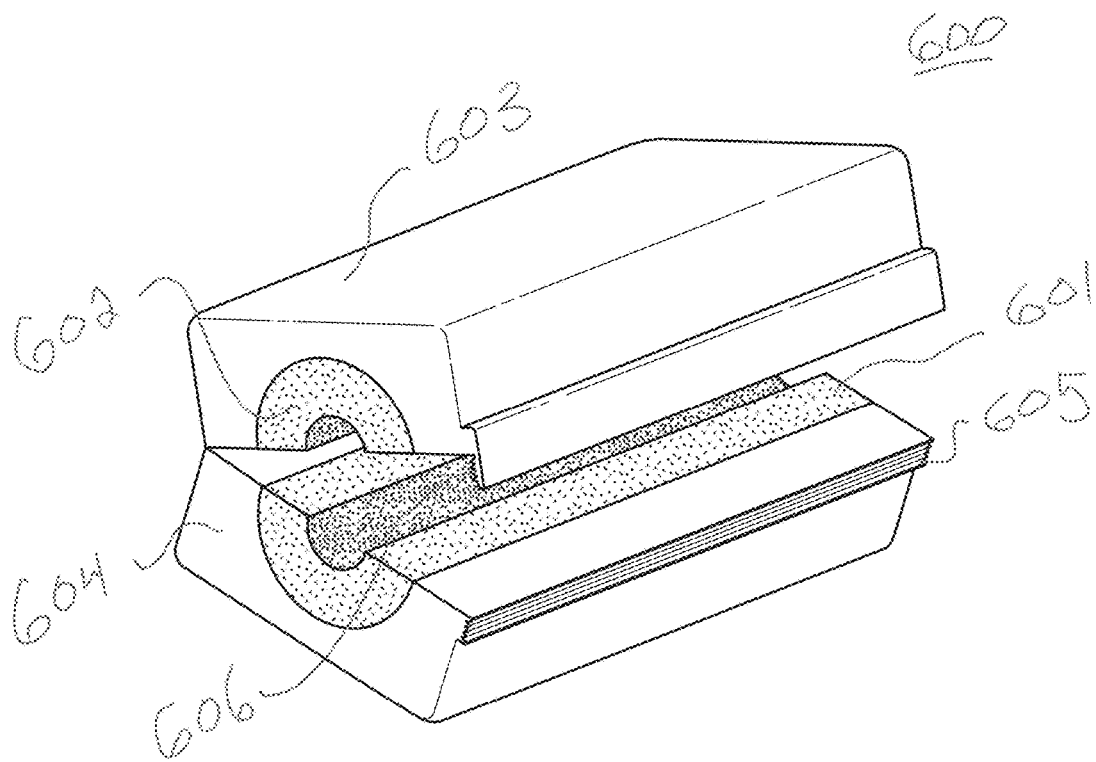
FIG. 6A shows universal coupler in open position.

FIG. 6A shows universal coupler in an open position. Coupler top structure 603 is used to provide mechanical compression to gasket material 602 using clasp 606. Bottom structure 604 is used to provide mechanical compression to bottom gasket material 601 using clasp 605. In open position, suction tubes of dissimilar sizes and interfaces may be placed in ends of the coupler, respectively.

Figure 6B:
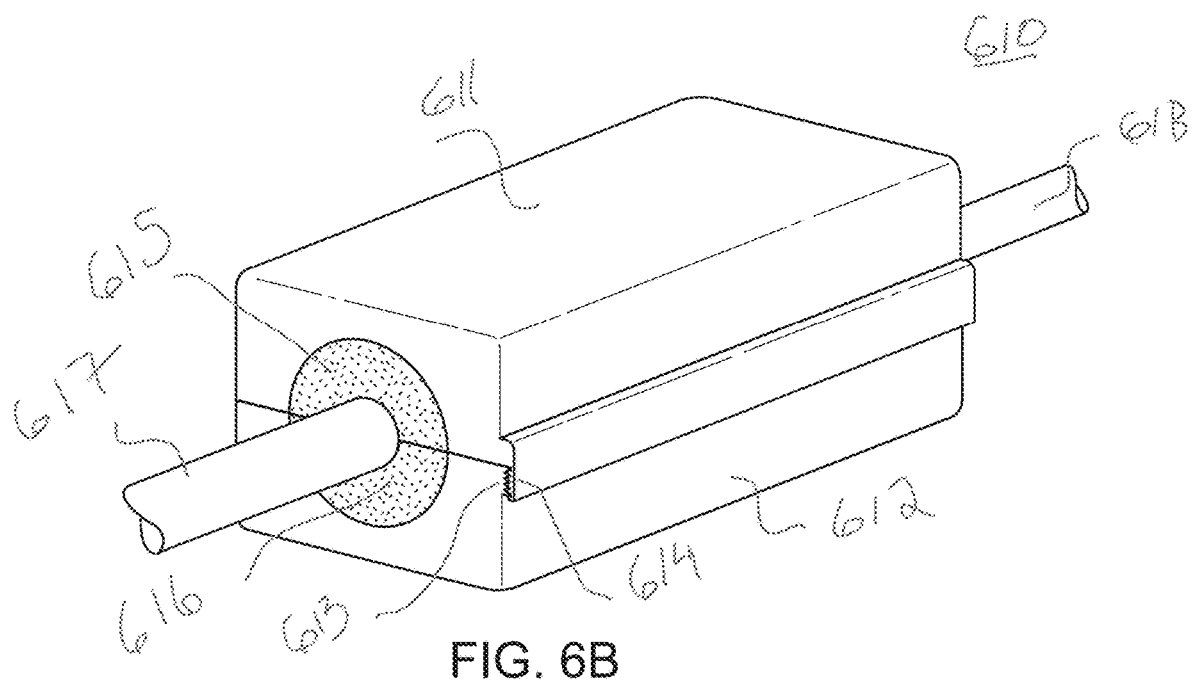
FIG. 6B shows universal coupler in closed position.

FIG. 6B shows a universal coupler in a closed position. In this closed position, bottom clasp 613 is composed of inter-locking teeth with top clasp 614. Such inter-locking teeth allow for mechanical compression between coupler top structure 611 and bottom structure 612 to form an air-tight seal around dissimilar suction tubes 617 and 618. The seal is maintained using gasket material 615 and 616 in compression around the is suction hoses. Such gasket material may be constructed from various materials known in the art, including closed cell foam or other material allowing an air-tight seal.

Figure 6C:
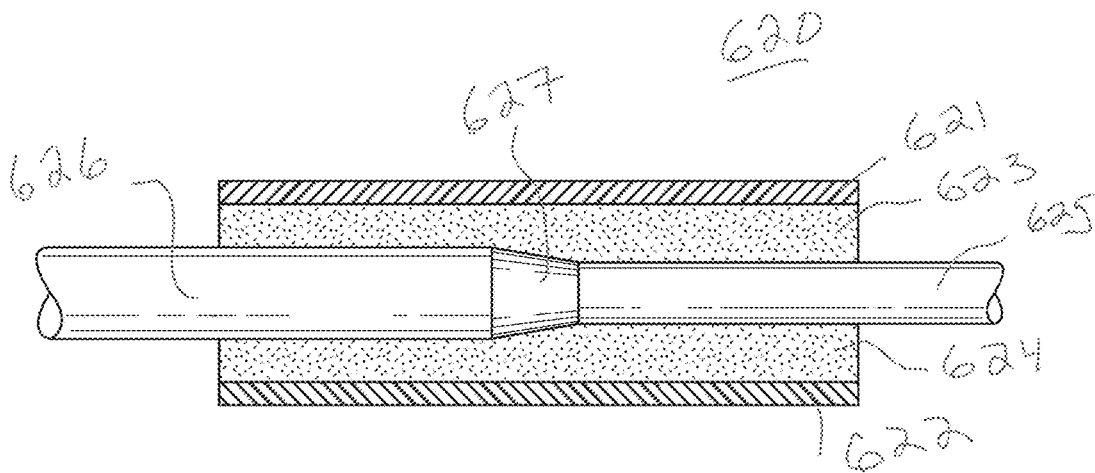
FIG. 6C shows cross section of universal coupler with hoses.

FIG. 6C shows a cross section of universal coupler with hoses. Coupler top structure 612 and coupler bottom structure 622 apply compressive force to gasket material 623 and 624 to form an air-tight seal around dissimilar hoses 626 and 625 with an air gap 627 between the two. While hoses 626 and 625 are depicted to be dissimilar in this Figure., this is not intended to be limiting and similar hoses may be interfaced in a similar way.

Figure 6D:
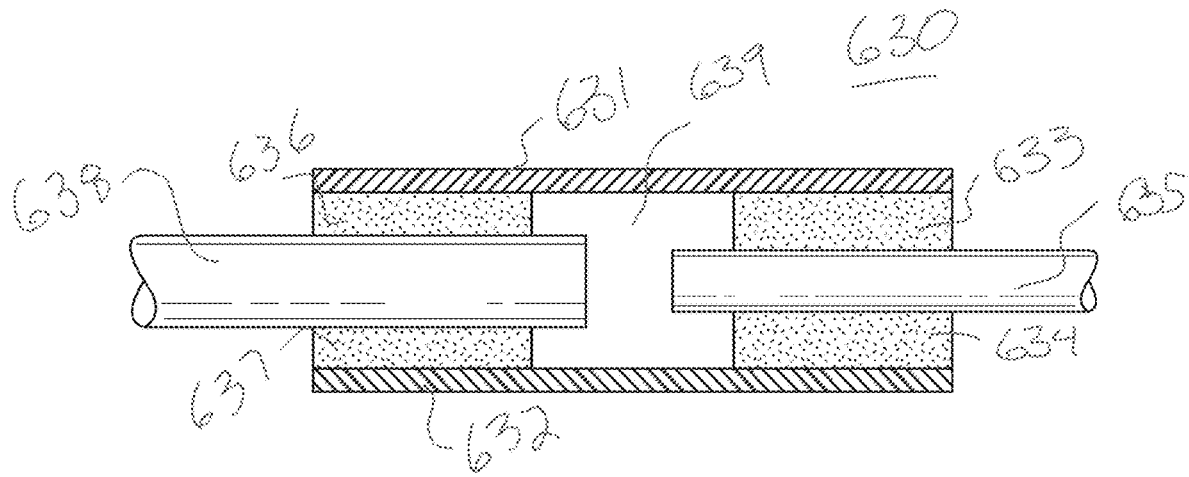
FIG. 6D shows alternative universal coupler embodiment cross section.

FIG. 6D shows a cross-section of an alternative universal coupler embodiment. As an alternative to the embodiment depicted in FIG. 6C, a top coupler structure 631 and bottom coupler structure 632 apply compressive force to gasket materials 636, 637, 633 and 634. Within the interfacing region between suction hose 638 and 635, an air gap with a small area not having gasket material is provided.

Figure 6E:
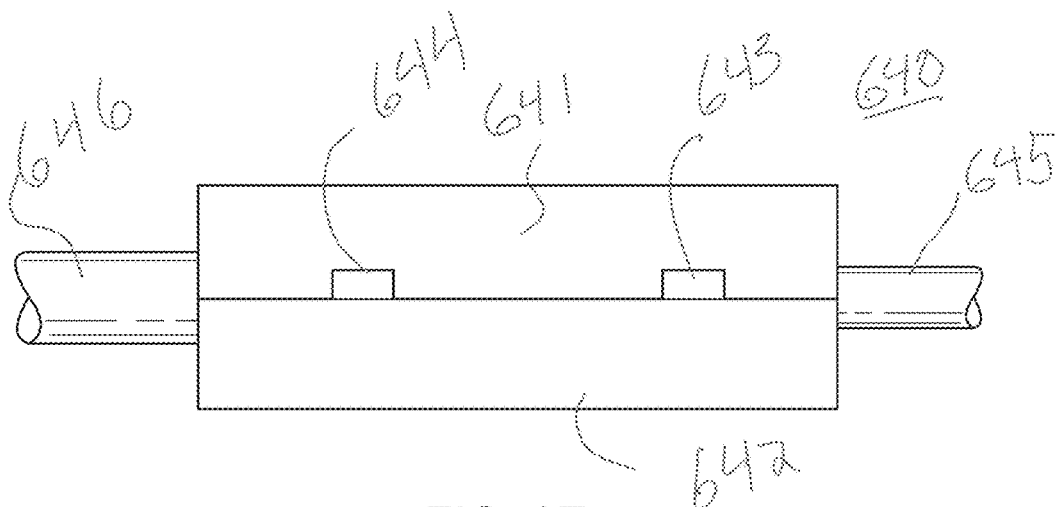
FIG. 6E shows universal coupler with alternative clasp.

FIG. 6E shows a universal coupler with alternative clasp. In this embodiment, universal coupler mechanical structure 641 and 642 may have compressive forces applied using more than a single clasp across the opening side of the coupler. Such clasps are shown as 644 and 643. It is intended that the internal gasket material be provided in any matter described to allow for the sealed interface between suction hoses 646 and 645.

In all of the FIGS. 6A through 6E, it is intended that one embodiment may have a sealed flexible joint between the top mechanical structure and bottom mechanical structure on the opposite side to the one or more clasps. Alternatively, one or more clasps may be used on any or all sides of the clasp mechanical structures.

Figure 7:
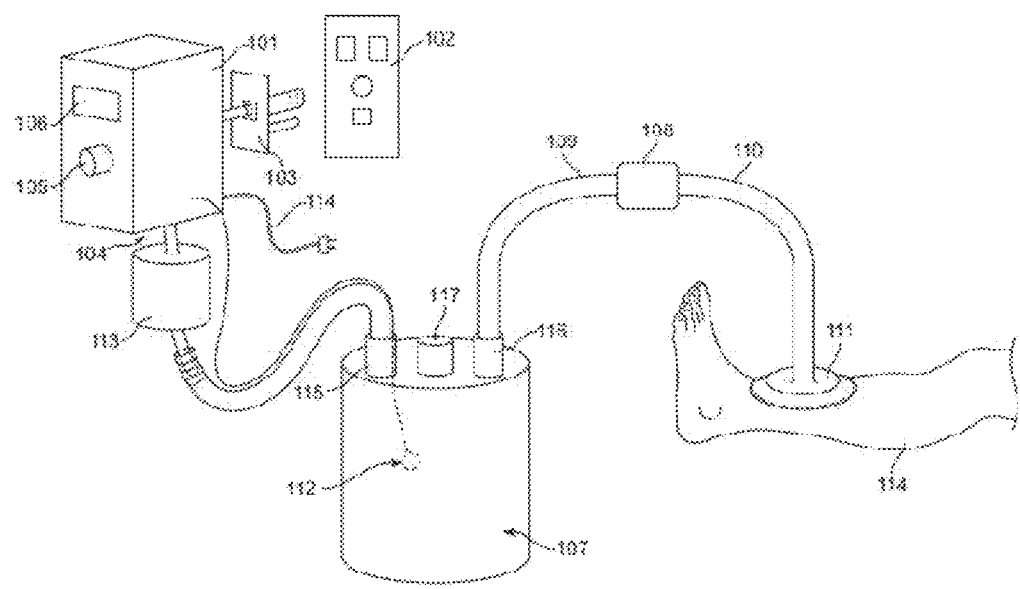
FIG. 7 is a diagram similar to FIG. 1 but showing another embodiment.

Referring to FIG. 7, a diagram of another embodiment similar to that of FIG. 1 is shown. Regulator unit 101 interfaces to wall suction source 102 via post probe 103. Regulator unit 101 provides regulated suction to sink port 104, interfacing to hose is assembly 113. The suction regulation control and other features may be set by control knob 105 and alarms and current status are displayed using display 106. Alternatively the suction regulation control features may be set using other interfaces such as wired or wireless network, using any number of protocol known to those skilled in the art. Sink port 104 interfaces to reservoir 107 via a tube assembly 113 including a safety trap, via reservoir port 115. The safety trap is used for catching liquids that have passed through the reservoir 107, to prevent the introduction of liquids into regulator unit 101. Reservoir unit 107 interfaces to universal coupler 108 via hose 109 and reservoir port 116. Universal coupler 108 provides for a common interface from the reservoir 107 and hose 109 to suction hose 110 provided by various manufactures with differing interfaces. In an alternative embodiment, universal coupler 108 may interface to reservoir 107 directly omitting and hose 109. Suction hose 110 interfaces to negative pressure dressing 111. In an alternative embodiment reservoir 107 and coupler 108 may be integral with regulator unit 101 including safety trap hose assembly 113, in some embodiments hose 109. Fluid level probe 112 is used to sense the fluid level in reservoir 107 and is monitored by regulator unit 101 and may alarm if fluid level is too high.

A standard vacuum port interface may be used as the port interface 102. Such an interface may conform to an ISO 10079-3:2009 compliant suction interface probe port, and are common to hospitals and treatment centers internationally. Although this is the standard interface for the embodiments described herein, other sources of suction may be used, such as interfaces to alternative pumps. This interface may also be used on a transportable pump to accommodate regulator unit 101 to allow for operation while detached from wall suction source during patient transport, shown in FIG. 8. The embodiment of FIG. 7 allows for decreased reliance on a separate suction source thus eliminating the additional cost of charges related to pump rental and reduced pump inventory requirements from various manufacturers.

Figure 8:
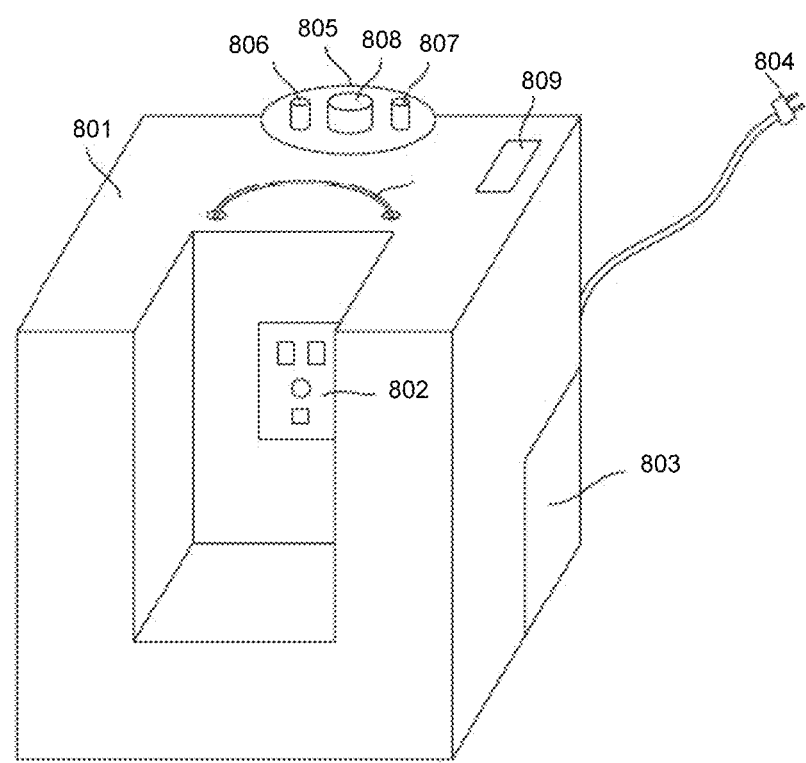
FIG. 8 shows an embodiment of a transport assembly.

FIG. 8 shows an embodiment of the transport assembly 801. Transport pump unit 801 includes a suction interface port 802 for interfacing to regulator unit 101. This port is 802 is compliant with specification for wall suction port 102 of FIG. 1. Transport unit 801 has a rechargeable battery 803 to power the unit when disconnected from wall power source. Charging of battery 803 would take place when power cord 804 is plugged into wall power. The pictured embodiment has a canister or reservoir 805 also common with FIG. 1 reservoir 107, in one embodiment. Such commonality allows for the reservoir 107 to be stored in transport unit 801 during transport for convenience as reservoir 805.

Figure 9:
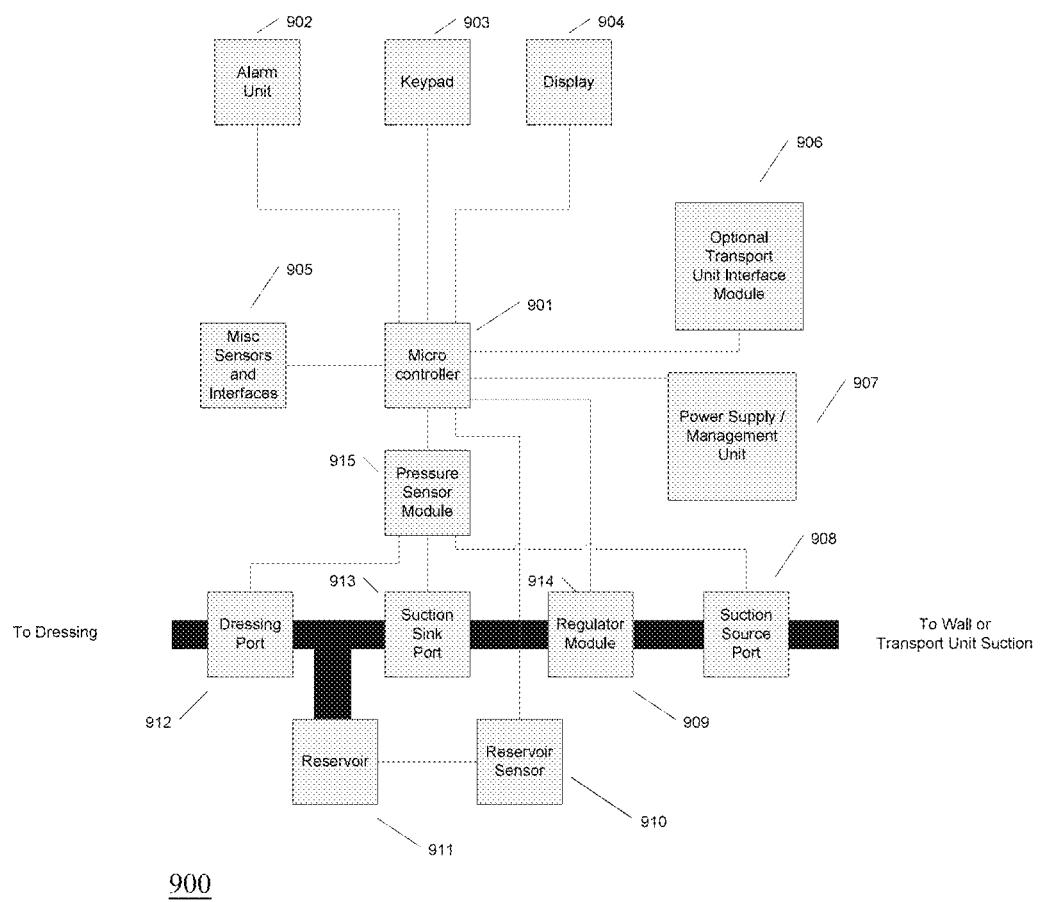
FIG. 9 is a functional block diagram of an embodiment of a regulator unit.

FIG. 9 is a functional block diagram of an embodiment of the functional blocks of regulator system 900 which includes the functionality of regulator unit 101, hosing assembly 113, reservoir 107, hosing assembly 109 and universal coupler 108. Micro controller 901 performs a number of functions of control and monitoring in unit 900 including interfacing with reservoir sensor 910 monitoring fluid levels within reservoir 911. Microcontroller 901 interfaces to regulator module 914 providing a control mechanism for pressure regulation between suction source post 908 and suction sink port 913. Microcontroller 901 further interfaces to pressure sensor module 915, which monitors at least one of dressing port 912, and suction sink port 913. Pressure sensor module 915 may further monitor suction source port 908. These monitoring points may be used to provide for pressure regulation as well as alarm conditions for out of tolerance pressure levels. Dressing port 912 includes the functionality of universal coupler 106 and interfaces to suction sink port 913 and reservoir 911 with hosing assembly 917. Suction sink port 913 interfaces to regulation module 914, which interfaces to suction source port 908. Connection 974 is used to interface to the wall suction or transport unit suction and comprises the functionality of probe 103. Microcontroller 901 further interfaces to alarm unit 902 used to provide audio or visual indications of alarm conditions. Keypad 903 interfaces to microcontroller 901 and provides for user input and configuration of the operational parameters. Including alarm tolerances, enabling and disabling alarm tolerances, suction level, and other parameters. Display 904 provides feedback to the user from microcontroller 901 of the status of regulator system 900. Misc sensors and interfaces module 905, provides for additional capabilities including but not limited to tilt sensors, temperature sensors, and may include additional interfaces including but not is limited to USB, Wi-Fi, Ethernet and serial and interfaces to microcontroller 901. Optional transport unit interface module 906 provides for an electrical interface with transport unit also pictured in one embodiment in FIG. 7. The electrical interface may include power and communications connections and provides for monitoring by microcontroller 901 of the conditions in transport unit 700. Power supply unit 907 provides for the monitoring and management of electrical power within regulator system 900 and interfaces with microcontroller 901 to provide for alarm capabilities.

Figure 10:
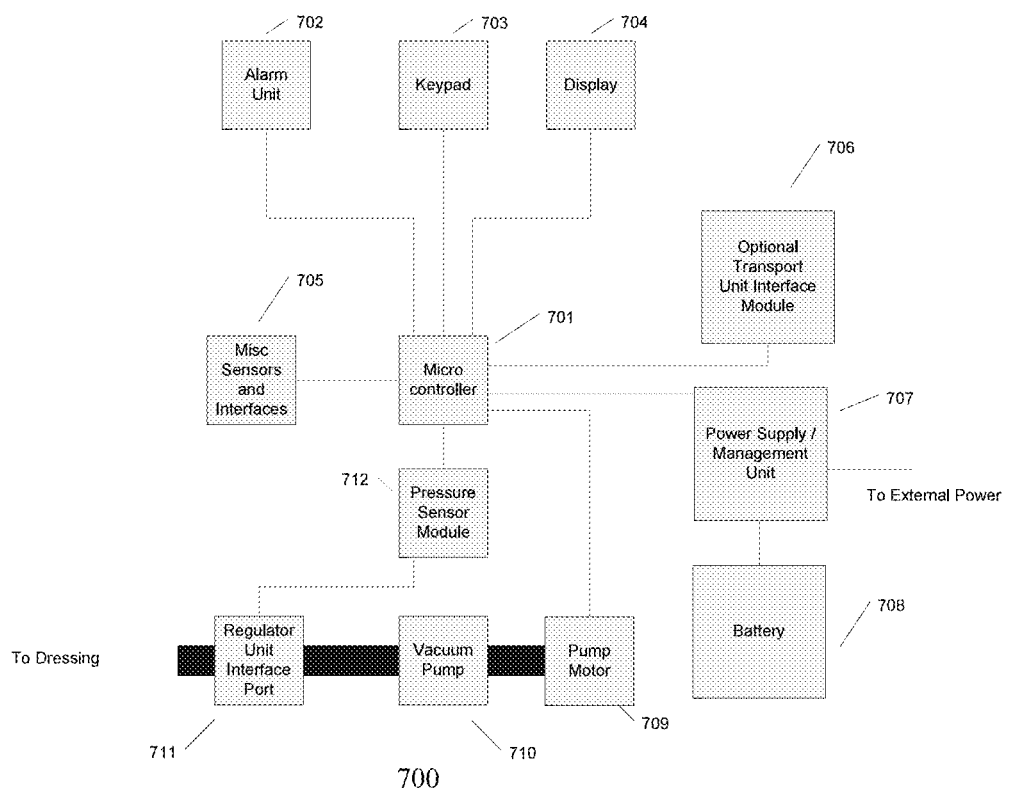
FIG. 10 is a function block diagram of an embodiment of a transport unit.

FIG. 10 is a function block diagram of an embodiment of a transport unit 700. Transport unit 700 includes microcontroller 701 which interfaces to pressure sensor module 712 which monitors pressure at the regulator unit interface port 711 in this embodiment. Microcontroller 701 further interfaces with pump motor 709 which interfaces to vacuum pump 710 producing suction through coupling 771 to regulator unit interface port 711. Regulator coupling 770 includes functionality and compatibility with wall suction interface 102 (ISO 10079-3:2009 compliant suction interface probe port). Microcontroller 701 may use information from pressure sensor module 712 for alarming purposes. Alarm unit 702, keypad 703, display 704 each interface with microcontroller 701 to provide for user input, alarm feedback, and status display to configure and monitor transport unit 700. Optional transport unit interface module 706 is compatible with optional transport unit interface module 906 in the regulator unit. Misc sensors and interfaces module 705, provides for additional capabilities including but not limited to tilt sensors, temperature sensors, and may include additional interfaces including but not limited to USB, Wi-Fi, Ethernet and serial and interfaces to microcontroller 701. Power supply management unit 707 interfaces to external power source using cable 758 and further interfaces to battery 708 and provides for monitoring, charging and management to of charging of the battery and interfaces with microcontroller 701.

The following is a non-limiting list of concepts believed to be significant.

An Improved Negative Pressure Wound Therapy Dressing

Universal Coupler for suction source with NPWT

External Fixator Adaptor for NPWT Dressing

Concept 1 is a negative pressure wound therapy sponge design having:

A non-wound contacting surface having a sealing layer preventing the passing of gas or liquids, The edges of the sponge being trim-able allowing for the correct fitting to a wound, and A sealing substance for sealing from the top the sponge, covering the non-sealed sides of the sponge, to the patents epidermis.

Also Concept 1, where the sealing substance is a tape including a protective layer, such protective layer being removed prior to application, and exposing an adhesive for the connecting of the tape to one or more of the top of the sponge, to the patient, and the another section of tape, and Where the adhesive is EKG lead adhesive or the like.

Also Concept 1, where a the top (sealed) side of the sponge include a suction hose interface port.

Also Concept 1 where a the top (sealed) side of the sponge is used to interface to a suction hose by a puncture in the sealed surface applied during application.

Concept 2 is a Regulation unit and assembly which includes:

a source port for connecting directly or indirectly to existing wall suction a dressing port for connecting either directly or indirectly to one or more NPWT Dressings a fluid reservoir associated with the regulation unit (either integral or via the sink port)

a Control interface, and/or an alarm function wherein the regulation unit regulates pressure between the wall suction port and one or more of the dressing port and a NPWT Dressing, and wherein the regulation includes maintaining a pressure profile at the one or more of the dressing port and a NPWT Dressing.

Concept 2, where the pressure profile is a constant pressure level

Concept 2, where the pressure profile is a predetermined pressure level which varies with time in a pre-determined manor Concept 2, where the pressure profile is dependent on external variables and/or wherein the external variables include one or more of The amount of suction resistance on one or more of the dressing port and a NPWT Dressing The fluid level in the reservoir The fluid drainage rate Input form an automated IV drug dispenser Input from a blood pressure monitoring device Information received via a wireless sensor, and/or Information received from another device such as Via a wireless receiver Via an Ethernet port Concept 2, where the alarm function Indicates loss of wall suction below a pre-determined threshold Indicates a loss of seal associated with one or more of the sink port, the NPWT Dressing interface, related interconnections.

Indicates a condition of an internal reservoir, and/or indicates a condition of an external reservoir where such indication is determined by use of an external detection apparatus Concept 2, where the Control interface performs one or more of the following functions:

Inputting a known pressure level or profile

Displaying information related to the current pressure and the pressure profile

Storing and/or retrieving pressure profiles

Retrieving alarm information

Retrieving monitored pressure regulation performance parameters

Status Display

Where the status display is a LCD display

Concept 3, which is Concept 2 where the interconnect between the dressing port and the NPWT dressing includes an adaptor.

Concept 3 where the adaptor is for adapting between a connection to the sink port and a connection to two more NPWT dressings with differing connection interfaces.

Concept 3, where two or more adaptors are interchangeable for adapting between a connection to the dressing port and a connection to one of two more NPWT dressings with differing connection interfaces.

Concept 3 where the adaptor is for adapting between a connection to the dressing port and a connection to two more NPWT dressings (multiple dressing interface).

Concept 2, wherein the reservoir is located internally to the regulation unit and assembly.

Concept 2, wherein the reservoir is located external to the regulator and control unit.

Concept 2, wherein the control functions may be accessed remotely Via an internet protocol (IP) based connection and/or via a web interface.

Concept 2, wherein the alarm functions may be accessed remotely via SMS, instant message, text message, email, or other electronic notification approach.

Concept 2, and including a Modular transport suction apparatus used interfacing to the Regulation unit via the source port and replacing the existing wall suction during transport operations.

What is claimed is:

1. A negative pressure wound therapy device adaptor, for interfacing to a suction source further comprising:
    a suction source interface structure comprising a compressible sealing structure;
    an adhesive for adhering a surface layer of a negative pressure wound therapy apparatus to at least a portion of the suction hose interface structure, and for providing a seal;
    wherein the device adaptor further has a lockable mechanically adjustable diameter for applying physical pressure to the suction source interface structure including the compressible sealing structure, to maintain negative pressure suction between the suction source interface structure and the negative pressure wound therapy apparatus.

2. A negative pressure wound therapy interface adaptor, for maintaining a seal between an external fixator and a surface layer of a negative pressure wound therapy apparatus, wherein the external fixator penetrates at least the surface layer of the negative pressure wound therapy apparatus, the interface adaptor comprising:
    an interface body comprising a compressible sealing structure;
    wherein the interface body is for receiving the external fixator and transferring negative pressure to the surface layer of the negative pressure wound therapy apparatus; and
    an adhesive for adhering the surface layer of the negative pressure wound therapy apparatus to at least a portion of the interface body; and
    wherein the interface body has a lockable mechanically adjustable diameter for applying physical pressure to the compressible sealing structure.

3. A negative pressure wound therapy interface adaptor apparatus for sealing between a surface layer of a negative pressure wound therapy apparatus and a surface layer penetrating structure, comprising:
    an adaptor body comprising a mechanically adjustable diameter for applying physical pressure to a sealing material;
    a first interface structure for maintaining a seal between the adaptor body and the surface layer penetrating structure within the mechanically adjustable diameter of the adaptor body, the first interface structure further comprising the sealing material; and
    a second interface structure for maintaining a seal between the adaptor body and the surface layer, around the surface layer penetrating structure.

4. The apparatus of claim 3 wherein the first interface structure further comprises a suction hose interface for interfacing a suction source to the surface layer of the negative pressure wound therapy apparatus.

5. The apparatus of claim 4 wherein the surface layer is at least a portion of a non-wound contacting layer of the negative pressure wound therapy apparatus.

6. The apparatus of claim 4, wherein the interface adaptor is configured for assembly with the negative pressure wound therapy apparatus during application of the negative pressure wound therapy apparatus to a wound surface.

7. The apparatus of claim 6, wherein the interface adaptor further comprises
    an adhesive for adhering the surface layer to at least a portion of the second interface structure.

8. The apparatus of claim 7, wherein the adhesive is a viscus or gel adhesive.

9. The apparatus of claim 7, wherein adhesive is applied in the form of a tape.

10. A negative pressure wound therapy apparatus comprising:
    a sponge layer for directly contacting a surface of a wound;
    a non-wound contacting layer for preventing passage of gas or liquid;
    wherein the non-wound contacting layer and the sponge layer are bonded together to form an integrated structure; and
    wherein one or more edges of the integrated structure are trimmable allowing for fitting to the wound; and
    further comprising
    a suction hose interface for interfacing a suction source to a surface layer of the integrated structure, wherein the suction hose interface is a prefabricated structure further comprising:
        an adhesive for adhering the surface layer to at least a portion of the suction hose interface;
        an interface adaptor, for receiving the suction source, and transferring negative pressure to the integrated structure;
        wherein the interface adaptor has a lockable mechanically adjustable diameter for applying physical pressure to a compressible sealing structure.

11. The apparatus of claim 3, wherein the one or more portions of the interface adaptor are configured to be sealed during application.

12. The apparatus of claim 3 wherein the surface layer penetrating structure further comprises an external fixator, and the first interface structure is an external fixator interface.

13. The apparatus of claim 12, wherein the interface adaptor is configured for assembly with the external fixator during application of the negative pressure wound therapy apparatus to a wound.

14. The apparatus of claim 12, wherein the interface adaptor further
    comprises an adhesive for adhering the surface layer to at least a portion of the second interface structure.

15. The apparatus of claim 14, wherein the adhesive is a viscus or gel adhesive.

16. A negative pressure wound therapy apparatus comprising:
    a sponge layer for directly contacting a surface of a wound;
    a non-wound contacting layer for preventing passage of gas or liquid;
    wherein the non-wound contacting layer and the sponge layer are bonded together to form an integrated structure; and
    wherein one or more edges of the integrated structure are trimmable allowing for correct fitting to the wound;
    further comprising:
    an external fixator interface for interfacing an external fixator to a surface layer of the integrated structure, and for maintaining a seal between the external fixator and the surface layer, wherein the external fixator penetrates at least the surface layer of the integrated structure;

wherein the external fixator interface is a prefabricated structure further comprising:
   an adhesive for adhering the surface layer to at least a portion of the external fixator; and
   an interface adaptor, for receiving the external fixator, and transferring negative pressure to the integrated structure;
   wherein the interface adaptor has a lockable mechanically adjustable diameter for applying physical pressure to a compressible sealing structure.

17. The apparatus of claim 12, wherein the external fixator comprises one or more of a pin, a wire, a screw, fixator, a nail, or other fastener.

18. An external fixator interface adaptor for interfacing an external fixator to a surface layer of a negative pressure wound therapy apparatus, and for maintaining a seal between the external fixator and the surface layer, wherein the external fixator penetrates at least the surface layer of the negative pressure wound therapy apparatus:
   wherein the negative pressure wound therapy apparatus comprises:
      a sponge layer for directly contacting a surface of a wound;
      a surface layer of a non-wound contacting layer for preventing passage of gas or liquid;
   wherein the external fixator interface comprises:
      an adhesive for adhering the surface layer to at least a portion of the external fixator interface adaptor; and
      a fixator interface, for receiving the external fixator, and transferring negative pressure to the surface layer;
      wherein the external fixator interface adaptor has a lockable mechanically adjustable diameter for applying physical pressure to a compressible sealing structure of the fixator interface.

* * * * *